United States Patent [19]
Maor

[11] Patent Number: 6,160,258
[45] Date of Patent: Dec. 12, 2000

[54] PATIENT SUPPORT FOR USE WITH MOBILE GAMMA CAMERA

[75] Inventor: Dov Maor, Haifa, Israel

[73] Assignee: GE Medical Systems Israel, Ltd., Tirat-Hacarmel, Israel

[21] Appl. No.: 09/473,327

[22] Filed: Dec. 28, 1999

Related U.S. Application Data

[63] Continuation of application No. PCT/IL98/00199, Apr. 28, 1998.

[51] Int. Cl.[7] ........................................ A61B 6/04
[52] U.S. Cl. .............................. 250/363.02; 250/363.02; 250/370.09
[58] Field of Search .................. 250/363.04, 363.02, 250/370.09

[56] References Cited

U.S. PATENT DOCUMENTS

| | | |
|---|---|---|
| 3,604,023 | 9/1971 | Lynch . |
| 3,818,516 | 6/1974 | Hopper et al. . |
| 4,156,145 | 5/1979 | Weatherholt . |
| 4,893,367 | 1/1990 | Heimreid et al. . |
| 5,261,406 | 11/1993 | MacKay et al. ................... 250/363.02 |
| 5,365,069 | 11/1994 | Eisen et al. ........................ 250/363.04 |
| 5,780,855 | 7/1998 | Pare et al. .......................... 250/363.04 |

FOREIGN PATENT DOCUMENTS 0 583 118  2/1994  European Pat. Off. .

*Primary Examiner*—Constantine Hannaher
*Assistant Examiner*—Andrew Israel
*Attorney, Agent, or Firm*—Fenster & Company Patent Attorneys, Ltd.

[57] ABSTRACT

A gamma camera arrangement and method for imaging a patient without moving the patient from the regular hospital bed to a patient carrier bed.

25 Claims, 2 Drawing Sheets

U.S. Patent     Dec. 12, 2000     Sheet 1 of 2     6,160,258

PATIENT SUPPORT FOR USE WITH MOBILE GAMMA CAMERA

RELATED APPLICATION

This application is a continuation of PCT application PCT/IL98/00199 filed Apr. 28, 1998, which designates the U.S.

FIELD OF THE INVENTION

This invention is concerned with diagnostic medical imaging and more particularly with mobile gamma camera arrangements used for such imagings.

BACKGROUND OF THE INVENTION

Many patients requiring gamma camera studies are confined to their beds. That is, the patient is so seriously ill that any movement of the patient from the bed puts the patient in jeopardy. In a great number of such cases where the patient is confined to bed, heart problems are the cause of the confinement. Accordingly, it is important to be able to acquire gamma camera images of the heart while the patient in the hospital bed with mobile and regular gamma cameras. Mobile gamma cameras are used in such cases.

Ideally the images should include single photon emission computerized tomographic (SPECT) images. To obtain good SPECT images of the heart, the camera must be able to rotate 180° about the patient to acquire unhindered views of patient while going from the left posterior oblique view (LPO) to the right anterior oblique view (RAO) of the heart and surrounding environment.

FIG. 1A illustrates more precisely what is meant by LPO, RAO and left anterior oblique (LAO) and right posterior oblique (RPO) views. The tomographic view of FIG. 1A shows a cross section of the patient 13 lying on his back on hospital bed 14. The heart 10 is shown on the left side of the tomographic image which means that the patient's feet are going into the paper and the patient's head is toward the viewer. The patient's torso is shown traversed by eight axes and directions which define the related views. The eight axes are the anterior axis 2, the right anterior oblique axis 3, the right axis 4, the right posterior oblique axis 5, the posterior axis 6, the left posterior oblique axis 7, the left axis 8 and the left posterior oblique axis 9. To acquire a tomographic image of the heart the detector head should rotate through the 180 degrees while it is as close as possible to the heart; i.e. from the LPO view to the RAO view.

FIG. 1A shows that when the patient is lying on his back, bed 14 interferes with the gamma rays during at least a portion of the scan.

The views illustrated in FIG. 1A should be acquired when the patient is lying so that no part of the range of patient observation by the camera is obstructed by the bed. It is desirable that the detector head to be as close as possible to the patient's heart during the acquisition of the views.

Cardiac SPECT is usually accomplished with 180° rotation of the camera detector about the patient. Angular rotations larger than 180° are also used. Modern reconstruction techniques enable rotations less than 180° to be used. Accordingly, whenever 180° rotation is referred herein more and less than 180° are also included.

Present day mobile gamma camera arrangements do not perform SPECT imaging because when the patient is on his back the view of the patient's heart when rotating from LPO to RAO is obstructed by the bed. Present day gamma camera arrangements, for SPECT, include an elongated, low gamma ray absorbence, patient support or bed. Thus, to be used the patient has to be moved from the regular hospital bed to the low gamma ray absorbence support of the camera arrangement.

The requirement to move the patient is also a serious detriment. The patient must be moved when using present day gamma cameras for SPECT imaging; since, it has not been possible to acquire the necessary views for a proper medical diagnosis if the patient remains in the hospital bed because of the interference of the regular hospital bed with the emitted gamma rays. The interference of the regular hospital bed with the acquisition of such images made it necessary in the past for the patient to be transferred to the imaging device that included a bed or support of low gamma ray absorbence.

Presently there are no known mobile gamma camera arrangements that can acquire satisfactory SPECT images of the bedridden patient's heart.

SUMMARY OF THE INVENTION

To obtain a SPECT image it is necessary for the gamma camera head or heads to rotate about the patient through 180 degrees. To obtain a good SPECT image of the patient's heart the detector should traverse the patient between the LPO view and the RAO view. That is when the camera is physically closest to the heart. However, part of the observation of the patient by the camera encounters the interference of the bed while the patient is lying on his back. Such interference precludes obtaining useful gamma camera images.

Accordingly, it is an object of some preferred embodiments of the present invention to provide gamma camera arrangements that can obtain LPO to RAO views of the bedridden patient's heart without having to move the patient from the hospital bed by moving the bed to the gamma camera. A related object of some preferred embodiments of the invention is to provide mobile gamma camera arrangements that can obtain LPO to RAO views of the bedridden patient's heart without having to move the patient from the bed by moving the gamma camera to the bed.

A further related object of the some preferred embodiments of invention is to provide gamma camera arrangements that can maintain the camera detector proximate the patient, without the bed obstructing the view while obtaining SPECT or static heart images.

A still further object of some preferred embodiments of the invention is to provide gamma camera arrangements that include an auxiliary support for use with the regular hospital bed to aid the patient in remaining in a position where the bed does not interfere with the imaging procedure. In this position the transverse axis of the patient is tilted to an angle of about 30–45 degrees to the surface of the bed. The auxiliary support is constructed of a material that has low absorbency of gamma rays.

A preferred embodiment of the present invention comprises a mobile gamma camera arrangement having a gantry that enables acquiring SPECT images by rotating the detector or head of the gamma camera around the patient so as to view 180 degrees of the patient while the head is in close proximity to the patient's heart and the patient remains in a hospital bed. Preferably, the views include both LPO and RAO views.

The primary purpose of the arrangement is to provide SPECT images of patients while they remain in their regular hospital beds. The invention is especially useful for imaging bedridden heart patients. It is difficult if not impossible for patients to position and support themselves so as to avoid the interference of the bed with the gamma rays being emitted by the patient.

To provide SPECT imaging, in accordance with a preferred embodiment of the invention, a patient support is provided that is sufficiently long to support the patient during acquisitions. Preferably the support is an inflatable cushion or is of a material that has very low and uniform absorption of gamma radiation, such as a plastic foam material for example and more preferably a hard plastic foam. The preferred embodiment is a wedge shaped patient support designed to enable the patient to be properly positioned in a restful manner. The wedge shaped support positions the patient so that there is no interference by the bed with the gamma rays for the required range of movement by the camera. Further, the patient is propped up by the support and is not under any strain during the imaging procedure. Hence among other benefits there is much less artifact causing patient movement during imaging.

In accordance with a preferred embodiment of the invention, the gantry supports a detector that is comprised of at least two heads mounted to be substantially perpendicular to each other. Such a detector arrangement is disclosed in U.S. patent application Ser. No. 07/755,649 filed on Sep. 6, 1991, the disclosure of which is incorporated herein by reference.

While a two headed arrangement with the heads being perpendicular to each other is preferred; it should be understood that the present invention is applicable to cameras having one or more detector heads. When a plurality of detector heads are provided they can be arranged at any one of a variety of selected angles to each other.

A dual detector, perpendicular head, utilizes only a 90 degree rotation to acquire 180 degrees of data. Accordingly, the gantry needs only be capable of 90 degrees of rotation to acquire a complete SPECT image. The dual detector head arrangement also provides the necessary image data in the shortest time period. Interference by the bed with the gamma rays is avoided when the patient support is used to maintain the bedridden or any other patient properly positioned during the imaging procedure. The patient's heart is then most proximate to and directly exposed to the detectors to enable views from LPO to RAO to be obtained in the shortest time and thus with a minimum of strain of the patient. The use of the support also minimizes patient movement which otherwise would create artifacts and image distortion.

In one preferred embodiment of the invention, the patient support is comprised of a hard foam wedge that is placed juxtaposed to the patient.

In another preferred embodiment of the invention, a wedge shaped inflatable pillow is used. The patient is positioned on an uninflated pillow which is then inflated. The inflated pillow positions and supports the patient to enable efficient acquisition of views from LPO to RAO. It should be understood that whenever acquisition of views from LPO to RAO is mentioned herein, the order of acquisition may be from RAO to LPO.

Further, while a wedge shape is desirable; the support can have other shapes, such as an elliptical shape. The support is preferably able to position the patient so that LPO to RAO views of the patient are acquired without interference by the bed with the gamma rays.

There is therefor provided, in accordance with a preferred embodiment of the invention, a gamma camera arrangement for use in imaging a patient while in a hospital bed, said arrangement comprising:

a detector arrangement mounted to scan said patient while in the hospital bed, and a patient support which supports the patient during the scan such that the hospital bed does not interfere with gamma radiation emitted by the patient.

In a preferred embodiment of the invention, the detector arrangement is comprised in a mobile gamma camera.

Preferably, the arrangement is operative to provide a scan suitable for constructing a single photon emission computerized tomographic (SPECT) image.

Preferably, the arrangement is operable to provide static gamma ray images, preferably an LPO view of the patient.

In a preferred embodiment of the invention, said detector arrangement has only a single detector head. In an alternative preferred embodiment of the invention, the detector arrangement comprises multiple detector heads. Preferably said detector arrangement comprises dual detector heads. In a preferred embodiment of the invention, the dual detector heads are perpendicular to each other. In an alternative preferred embodiment of the invention, the angle between the dual detector heads is variable.

In a preferred embodiment of the invention, the patient support has low gamma radiation absorbence. Preferably, the patient support is shaped to support the patient at an angle to the bed to prevent the bed from interfering with gamma radiation emitted by the patient. Preferably, the patient support is shaped so as to allow the detector head to provide an LAO view of the heart of the patient without the bed interfering with the radiation emitted by the patient.

In one preferred embodiment of the invention, the patient support is wedge shaped. Alternatively, the patent support has a generally elliptic shape.

In a preferred embodiment of the invention, the patient support is produced from a foam plastic. Alternatively, the patient support is an inflatable pillow.

In a preferred embodiment of the invention, the patient support is substantially rigid. In a preferred embodiment of the invention, the support is at least 100 cm long. Alternatively the patient support is at least 150 cm long. In a preferred embodiment of the invention, the patient support is between 150 and 200 cm long.

There is further provided, in accordance with a preferred embodiment of the invention a method of nuclear medicine imaging of a patient in a hospital bed which absorbs gamma radiation, comprising:

providing a patient supported on his back and lying in a bed which absorbs gamma radiation; and acquiring an LPO nuclear medicine image, preferably a cardiac image, of the patient.

There is further provided, in accordance with a preferred embodiment of the invention a method of nuclear medicine imaging of a patient in a hospital bed which absorbs gamma radiation, comprising:

providing a patient supported on his back and lying in a bed which absorbs gamma radiation; and acquiring a SPECT image, preferably a cardiac SPECT image of the patient.

Preferably the SPECT image is generated from data including data from an LPO view.

In accordance with a preferred embodiment of the invention, the method includes turning the patient such that the bed does not interfere with a LPO view, preferably by placing a support under the left side of the patient.

BRIEF DESCRIPTION OF THE DRAWINGS

The above named and other objects and features of the present invention will be best understood from a reading of the following detailed description of the invention in conjunction with the accompanying drawings; in which.

DETAILED DESCRIPTION OF PREFERRED EMBODIMENTS OF THE INVENTION

Figure 1A:
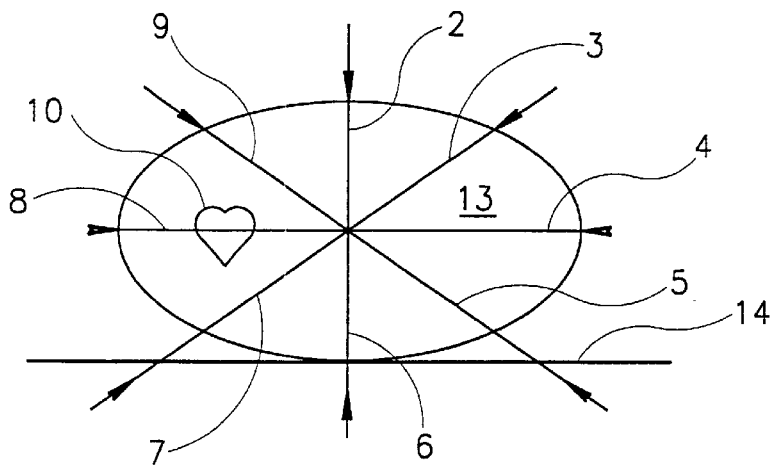
FIGS. 1A and 1B are cross-sectional views of the patient through the heart illustrating for definition purposes the anterior, right anterior oblique, right, right posterior oblique, posterior, left posterior oblique, left and the left anterior oblique views, without and with an auxiliary patient support respectively.
Figure 1B:
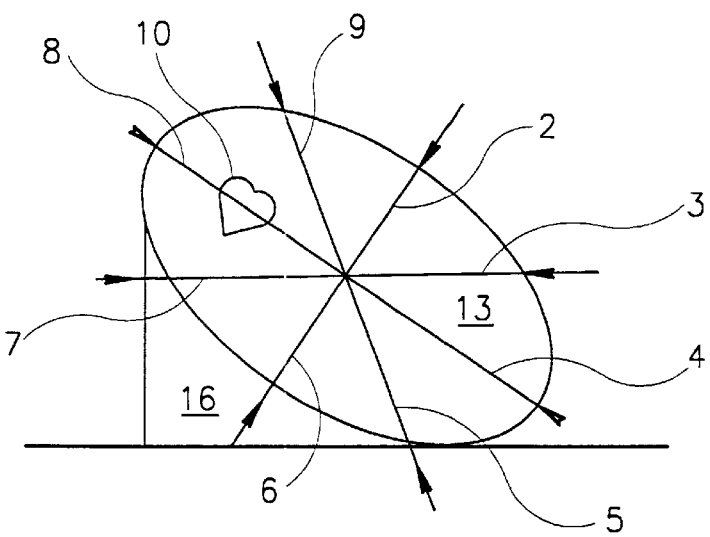

The view of FIG. 1B illustrates how an auxiliary patient support 16 positions the patient so that the bed does not interfere with the gamma rays throughout the 180 degree SPECT scan.

Figure 2:
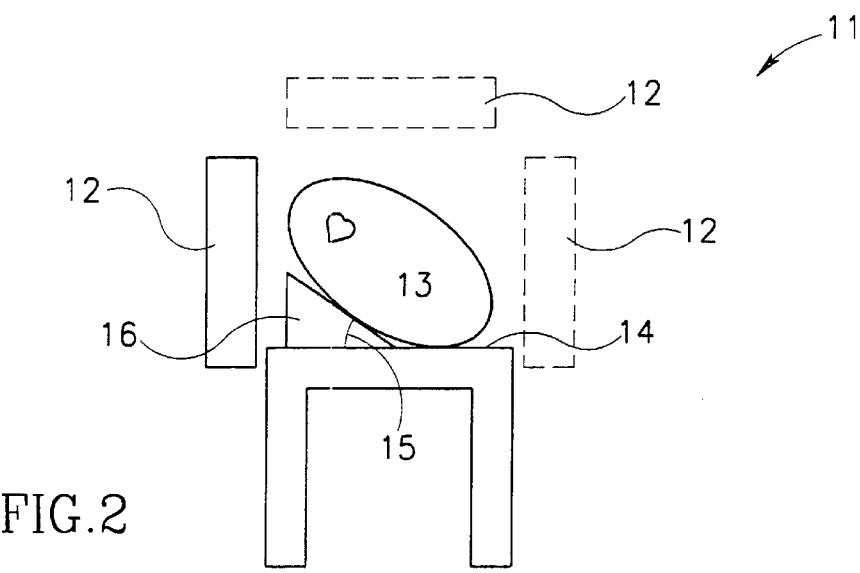
FIG. 2 is a simplified illustration of the use of the auxiliary patient support as a single detector head is rotated through 180 degrees about the patient, in accordance with a preferred embodiment of the invention.

FIG. 2 shows the relationship of a single head gamma camera system to a patient in a regular hospital bed, during SPECT imaging, in accordance a preferred embodiment of the invention. A gantry which facilitates the movement of the head about the patient is not shown in FIG. 2. The patient is propped up in the bed with auxiliary patient support 16. The support assures that the patient is turned and elevated to remove interference of the bed with the gamma radiation over the desired range of movement of the camera and enables the patient to rest while properly positioned with the least amount of discomfort and with maximum stability.

More particularly a gamma camera system 11 includes a detector head 12 shown in a first position in the solid line drawing of the head. The first position enables a left posterior oblique image of the heart or the acquisition of image data for the beginning of a SPECT image to be acquired. Patient 13 is shown lying on bed 14. The patient is propped on auxiliary patient support 16. The support maintains the patient in comfort with the heart exposed to enable the LPO view of the heart of the detector head 12 in its first position. In addition to supporting the patient while he rests on his side, the support also assures that the bed does not interfere with the gamma rays coming from the patient and helps to keep unwanted patient motion to a minimum. In a preferred embodiment of the invention the support comprises a hard foam wedge. The angle of the wedge is preferably sufficiently large to avoid interference by the bed with the gamma rays so that a good left posterior oblique view is acquired with the detector head in the first position.

Foam support 16, in a preferred embodiment of the invention, is wedge shaped having a 30–45 degree angle and is about 15–20 cm in height and approximately as long as the patient. Thus, a support that is approximately 200 cm in length could be sufficient. Alternatively, a support for the torso, approximately 100 cm in length may be used.

In another preferred embodiment of the invention, a wedge shaped inflatable pillow is used. The patient is positioned on an uninflated pillow which is then inflated. The inflated pillow positions and supports the patient to enable efficient acquisition of views from LPO to RAO. It should be understood that whenever acquisition of views from LPO to RAO is mentioned herein, the order of acquisition may be from RAO to LPO.

Further, while a wedge shape is desirable; the support can have other shapes, such as an elliptical shape. The support is preferably able to position the patient so that LPO to RAO views of the patient are acquired without interference by the bed with gamma rays.

A second position shown of head 12 is shown in FIG. 2, in which the head is positioned above patient 13 at an angle 90 degrees from the first position. During rotation of the head, a good anterior view of the heart is acquired while the patient is propped up with the wedge like support. The second position shown is in the path of the rotation of the head about the patient during the acquisition for the SPECT scan. The head in the second position is illustrated in dashed line form.

A third position of the head 12 is shown in FIG. 2 in which the head is situated at the right side of the patient 13 (i.e., on the opposite side of the patient from the side of the first position). The third position is 180 degrees removed from the first position and is also illustrated in dashed line form. The third position (RAO) is used to complete the acquisition of the SPECT image data. Thus, with a single head system, 180 degrees of rotation are required to acquire the data for a SPECT image. It should be understood that while three different static positions of the head are shown, in reality preferably the head rotates on a continuous basis and acquire image data at a large number of intermediate positions of the head.

The arrangement of FIG. 2 is also well suited for static imaging. In static imaging the gamma camera is positioned to acquire static views of the heart sighting along the LPO axis, the left axis and the RAO axis. The arrangement enables good views of the heart with the camera detector as close as possible to the heart.

Figure 3A:
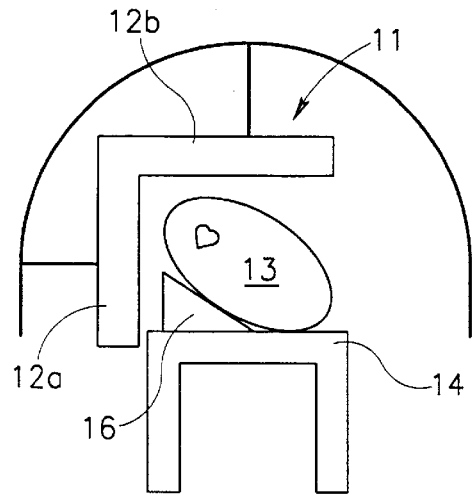
FIG. 3A shows a dual detector head arrangement with dual heads in a first position, in accordance a preferred embodiment of the invention.
Figure 3B:
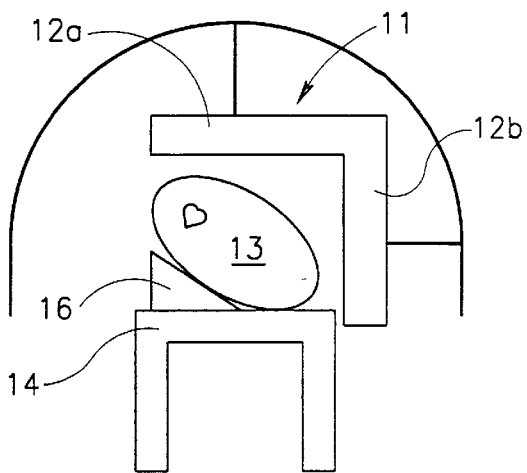
FIG. 3B shows the dual detector head arrangement with the dual heads in a second position, rotated 90° from the first position of FIG. 3A.

FIGS. 3A and 3B illustrate an embodiment of the invention in which a detector 11 comprises two heads 12a and 12b arranged to be perpendicular to each other. With such an arrangement a SPECT image can be acquired with only 90 degrees of rotation. More particularly FIG. 3A shows the two heads 12a and 12b in a first position. In this position head 12a is positioned to acquire data starting from a left posterior oblique view of the heart of the patient 13. During the image acquisition the patient is propped up on support 16 while the patient is in the regular hospital bed 14. At the same time head 12b is positioned to acquire data starting from above the patient. A gantry (not shown in this figure) rotates the heads about the patient 13 until the position of FIG. 3B is arrived at.

In FIG. 3B head 12a is shown acquiring data from above the patient. Head 12b, in the position shown in FIG. 3B, is located 180 degrees removed from head 12a of FIG. 3A. Thus, the dual head arrangement of FIGS. 3A and 3B acquires 180 degrees of information during 90 degrees of rotation using a mobile gamma camera arrangement.

While heads 12a and 12b are shown as being a single unit, it should be understood that within the scope of the invention, heads 12a and 12b can be separate units, linked to move together. It is desirable that the two heads have the capability of acquiring enough data for a SPECT image during only 90 degrees of rotation. Thus, the imaging time is substantially reduced as compared to imaging time when using the single head version of the invention.

Figure 4:
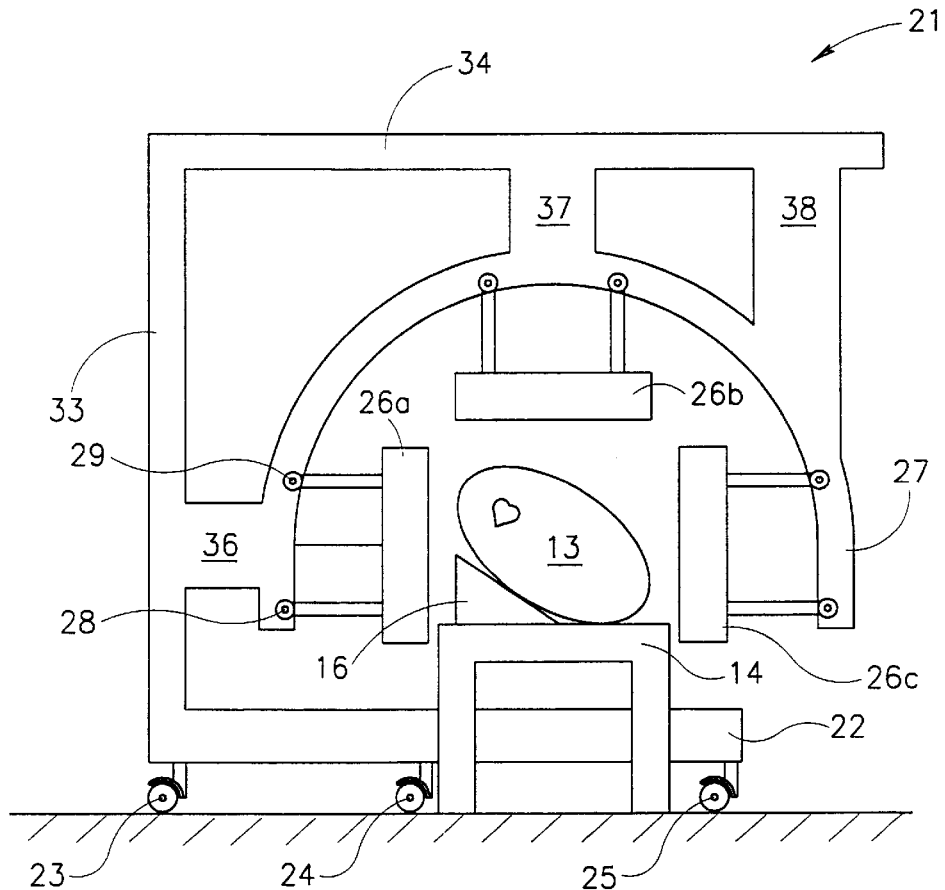
FIG. 4 is a simplified illustration of a gantry for a mobile camera arrangement, in accordance a preferred embodiment of the invention, for use in imaging a patient in a regular hospital bed, showing 180 degrees of rotation of the detector head.

FIG. 4 shows the mobile gantry arrangement for imaging patients in their hospital beds, in accordance with a preferred embodiment of the invention. A gantry 21 is shown as comprising a base portion 22 mounted on wheels such as wheels 23–25. In a preferred embodiment the wheels are electrically driven as is well known in the art. Alternatively, the gantry is stationary and the bed is rolled to the camera instead of the other way around.

A detector head 26, is preferably coupled to an arcuate or semi-circular like track indicated at 27. The head is shown at a starting position imaging the LPO of the SPECT scan as 26a, at an intermediate position as 26b and at a final position of the SPECT scan as 26c. Head 26 is preferably coupled to track 27 by means such as trolley wheels indicated at 28 and 29 or by other suitable means known in the mechanical arts. The wheels are preferably electrically driven such that head 26 may be electrically rotated from position 26a to 26c. Track 27 is preferably supported by a vertical column 33 of the gantry through a cantilevered arm 34. The vertical column rises from a base 22.

Track 27 is supported from the column 33 and the cantilevered arm 34 by a horizontal support arm 36 and two vertical support arms 37 and 38 respectively. The support arms are connected to the column, the cantilevered arm and the semi-circular track with any well known fastening means such as by welding or through the use of fasteners (not shown).

It should be understood that gantry 21 is operated to rotate a detector arrangement around the propped up patient along track 27 which may be gear like so that a single head can cover the 180 degrees needed for SPECT imaging.

Alternatively, gantry 21 can support a dual head detector arrangement such as that shown in FIGS. 3A and 3B, When a dual head arrangement is used only 90 degrees of rotation are required for a SPECT image.

In other preferred embodiments of the invention, other means and methods of rotating the detector head or heads, as are well known in the art may be used.

In an alternative preferred embodiment of the invention, track 27 is supported by an elevator like arrangement, as known in the prior art, for raising and lowering the track to enable maintaining the detector arrangement as close as feasible to the patient during imaging when acquiring static images; and during rotation of the detectors around the patient when acquiring SPECT images. The elevator arrangement may be a mechanical device such as a motorized screw thread elevator arrangement, or a hydraulic or pneumatic arrangement. Thus any type of automatic elevator arrangement known to those skilled in the art could be used within the scope of the invention.

In operation the mobile gamma camera arrangement of the invention is well suited to image patients (including SPECT imaging) while in their hospital beds and especially bedridden patients who are restricted from moving from the bed and who would be stressed to lie unsupported on their sides during a gamma camera imaging procedure. The patient is propped on the wedge to remove him from the location where the hospital bed interferes with the gamma radiation for the required imaging directions. Mobile gamma camera arrangements in accordance with preferred embodiments of the invention, are generally capable of performing either or both static scans and SPECT scans while the patient remains in the hospital bed.

While the invention has been described using specific embodiments; it should be understood that the present invention should not be construed as being limited to such embodiments, but rather should be construed according to the following claims:

What is claimed is:

1. A gamma camera arrangement for use in imaging a patient while in a regular hospital bed as distinguished from a patient carrier bed, said arrangement comprising:
    a detector arrangement mounted to scan said patient while in the regular hospital bed; and
    a patient support which supports the patient during the scan in a position such that the regular hospital bed does not interfere with gamma radiation emitted by the patient.

2. The gamma camera arrangement of claim 1 wherein the detector arrangement is comprised in a mobile gamma camera.

3. The gamma camera arrangement of claim 1 wherein the arrangement is equipped to provide a scan suitable for constructing a single photon emission computerized tomographic (SPECT) image.

4. The gamma camera arrangement of claim 1 wherein the arrangement is equipped to provide static gamma ray image.

5. The gamma camera arrangement of claim 3 wherein said image includes data acquired from an LPO view.

6. The gamma camera arrangement of claim 1 wherein said detector arrangement has only a single detector head.

7. The gamma camera arrangement of claim 1 wherein said detector arrangement comprises multiple detector heads.

8. The gamma camera arrangement of claim 7 wherein said detector arrangement comprises dual detector heads.

9. The gamma camera arrangement of claim 8 wherein said dual detector heads are perpendicular to each other.

10. The gamma camera arrangement of claim 8 wherein the angle between the dual detector heads is variable.

11. The gamma camera arrangement of claim 1 wherein the patient support has low gamma radiation absorbence.

12. The gamma camera arrangement of claim 1 wherein the patient support is shaped to support the patient at an angle to the bed to prevent the bed from interfering with gamma radiation emitted by the patient.

13. The gamma camera arrangement of claim 1 wherein the patient support is shaped so as to allow the detector head to provide an LAO view of the heart of the patient without the bed interfering with the radiation emitted by the patient.

14. The gamma camera arrangement of claim 1 wherein said patient support is produced from a foam plastic.

15. The gamma camera arrangement of claim 1 wherein the patient support is substantially rigid.

16. A gamma camera arrangement for use in imaging a patient while in a hospital bed, said arrangement comprising:
    a detector arrangement mounted to scan said patient while in one hospital bed; and
    a wedge-shaped patient support which supports the patient during the scan such that the hospital bed does not interfere with gamma radiation emitted by the patient.

17. A gamma camera arrangement for use in imaging a patient while in a hospital bed, said arrangement comprising:
    a detector arrangement mounted to scan said patient while in the hospital bed; and
    a generally elliptically shaped support which supports the patient during the scan such that the hospital bed does not interfere with gamma radiation emitted by the patient.

18. A gamma camera arrangement for imaging a patient while the patient is in a hospital bed, said arrangement comprising:

a detector arrangement mounted to scan said patient while in the hospital bed;

a patient support which supports the patient during the scan such that the hospital bed does not interfere with gamma radiation emitted by the patient; and wherein the patient support is an inflatable pillow.

19. A gamma camera arrangement for imaging a patient while in a hospital bed, said arrangement comprising:

a detector arrangement mounted to scan said patient while in the hospital bed; a patient support which supports the patient during the scan such that the hospital bed does not interfere with gamma radiation emitted by the patient; and wherein said patient support is at least 100 cm long.

20. A gamma camera arrangement for imaging a patient while in a hospital bed, said arrangement comprising:

arrangement mounted to scan said patient while in the hospital bed;

a patient support which supports the patient during the scan such that the hospital bed does not interfere with gamma radiation emitted by the patient; and wherein said patient support is at least 150 cm long.

21. A gamma camera arrangement for imaging a patient while in a hospital bed, said arrangement comprising:

arrangement mounted to scan said patient while in the hospital bed; a patient support which supports the patient during the scan such that the hospital bed does not interfere with gamma radiation emitted by the patient; and wherein said patient support is at least 200 cm long.

22. A method of nuclear medicine imaging of a patient in a regular hospital bed which absorbs gamma radiation, said regular hospital bed being distinct from a patient carrier bed normally used when imaging a patient;

scanning said patient to detect gamma radiation emitted by the patient; and providing a support for the patient during the scanning such that the patient is positioned to enable the scanning substantially without interference by the hospital bed in the detection of the gamma radiation emitted by the patient.

23. The method of claim 22 and acquiring an LPO image of the patient.

24. The method of claim 23 wherein the acquired image is a cardiac image.

25. The method of claim 22 and acquiring a cardiac SPECT image.

* * * * *